United States Patent
Caskey et al.

(10) Patent No.: US 6,542,235 B1
(45) Date of Patent: Apr. 1, 2003

(54) SYSTEM AND METHOD OF THREE-DIMENSIONAL INSPECTION OF CIRCULAR PARTS

(75) Inventors: Gregory T. Caskey, Holland, MI (US); Angelo E. Ciccone, Chicago, IL (US)

(73) Assignee: Lakeshore Vision & Robotics, L.L.C., Zeeland, MI (US)

( * ) Notice: Subject to any disclaimer, the term of this patent is extended or adjusted under 35 U.S.C. 154(b) by 0 days.

(21) Appl. No.: 09/561,022

(22) Filed: Apr. 28, 2000

(51) Int. Cl.[7] .................. G01B 11/00; G01B 11/24; G01N 21/00
(52) U.S. Cl. .............. 356/394; 356/237.1; 356/601; 348/129
(58) Field of Search .................. 356/394, 398, 356/601, 603, 612, 614, 237.1, 429–431; 250/223 R, 559.2, 559.08, 559.22; 382/142, 149, 143, 147, 150, 154; 348/125, 126, 129, 130

(56) References Cited

U.S. PATENT DOCUMENTS

| | | | | |
|---|---|---|---|---|
| 4,286,880 A | * | 9/1981 | Young | 356/431 |
| 4,971,445 A | * | 11/1990 | Sato et al. | 356/376 |
| 5,259,513 A | * | 11/1993 | Tahkanen et al. | 209/566 |
| 5,495,337 A | * | 2/1996 | Goshorn et al. | |
| 6,061,126 A | * | 5/2000 | Yoshimura et al. | 356/237.1 |

* cited by examiner

Primary Examiner—Hoa Q. Pham
(74) Attorney, Agent, or Firm—Van Dyke, Gardner, Linn & Burkhart, LLP (57) ABSTRACT

An inspection system for inspecting circular parts of the present invention includes a light source, a camera, and a computer, which is in communication with the camera and has stored therein known good part profile data. The light source is for directing light onto the part to be inspected, with the camera generating profile signals in response to the light on the part. The computer receives the profile signals from the camera and assembles the profile signals into a height image of the part and, further, compares the height image with the known good part profile data to determine whether the part is acceptable or unacceptable.

32 Claims, 4 Drawing Sheets

Flipped parts are conveyed to a second system for data acquisition and analysis similar to the aforementioned method.

↓

Acceptable parts travel to end of conveying means and are available for packing.

Unacceptable parts are removed as for the first analysis stage.

FIG.3A

SYSTEM AND METHOD OF THREE-DIMENSIONAL INSPECTION OF CIRCULAR PARTS

TECHNICAL FIELD AND BACKGROUND OF THE INVENTION

The present invention relates to inspection of parts and, more particularly, to quality control inspection of circular parts. Heretofore, quality control of circular parts, such as seals, diaphragms, wiring protection through holes, and the like, has been difficult and tedious. Parts that fall into this category typically include, but are not limited to, transmission seals, grommets, actuator diaphragms and the like. These products may be metal, coated metal, plastic or polymeric materials, composite materials and the like, or a combination thereof.

Conventional inspection methods are typically manual and are, consequently, labor intensive. Human inspectors look at each part individually and visually locate cosmetic, Material or other defects. This process is subject to fatigue and inattentiveness, and so is unreliable and inconsistent. In the automotive industry, quality standards are increasingly demanding and consequently make increasing demands on quality control departments of suppliers. The inability of human inspectors to reach the high production levels while maintaining the levels of quality required by discerning customers, such as automotive companies, coupled with the repetitive motion injuries frequently sustained in such operations, make automated inspection more a requirement than an option.

The problem the suppliers face is a lack of devices capable of inspecting for defects that humans can, in fact, find. Duplication of human inspection is difficult. Even machine vision systems using ordinary camera and computer technology find it hard to detect these defects since cameras look only at the two-dimensional projections of these defects.

Even with ordinary machine vision and other methods, manufacturers are dissatisfied with many automated inspection approaches and seek alternatives to what is commercially available. Two-dimensional (2-D) machine vision is one of the more advanced means of inspection. But, as noted above, even this is thought by some manufacturers to be inadequate. The rationale is that cosmetic and other types of defects can be detected by 2-D machine vision only if the defect reflects light differently from the surrounding material. This is difficult to assure. While three-dimensional (3-D) methods have been developed, current three-dimensional methods are regarded as slow. Although the newly developed three-dimensional methods appear to offer high resolution, inspection times are considerably longer than the one part per second or two part per second that manufacturers want.

Consequently, new tools are needed to approach the level of inspection that can be achieved using human inspectors, while maintaining high levels of reliability and consistency. Furthermore, it would be highly desirable for the method and apparatus using three-dimensional methods to inspect parts at a rate of one to two parts per second. In addition, in order for the method or apparatus to be fully utilized, the method and apparatus needs to be easy for manufacturing engineers to inspect a variety of parts that include preprogram inspection parameters. In addition, ideally the system should not permit operators to change program inspection parameters; instead, operators should only be able to call up a part number and have all the associated parameters loaded automatically.

SUMMARY OF THE INVENTION

According to the present invention, an inspection system includes hardware and software to inspect both sides of circular objects and, preferably, inspect both sides of circular objects at rates approaching one part per second. Such parts that can be inspected using the system of the present invention include grommets, diaphragms, rotary seals, and the like.

According to one form of the invention, the inspection system includes a camera, a computer which is in communication with the camera, and a light source. The light source is energized in order to project light onto a part which is to be inspected and viewed by the camera. The camera generates profile signals in response to the light on the part. The computer, which receives the profile signals from the camera, is preprogrammed to gather the profile signal data and analyze the profile signal data by comparison to known good part data. In this manner, by comparing the data from the inspected part to the known good part data, the system can detect defects in the part.

In one aspect, the structured lighting light source generates a structured light, for example, a line light. In the preferred form, the light source comprises a laser line generator. Preferably, the line light is projected down onto the part while the camera views the line light offset at an angle, for example, an angle in a range of approximately 30–60° from the line light.

In another aspect of the invention, the inspection system includes a second light source and a second camera. The second light source directs light onto a second side of the part. The second camera generates profile signals for the second side of the part, which are similarly analyzed by the computer. In the further form, the inspection system includes a second computer, such that each computer is associated with a camera, preferably with the first and second computers being networked. In preferred form, the cameras comprise high speed cameras, such as analog or digital cameras. Further, the high-speed camera may include addressable or non-addressable configurations. These camera forms are known to those skilled in the art of machine vision.

In other forms, the structured lighting light source may generate single or multiple lines or other geometries of projected structure light, including, for example, dots, radial lines, chevron lines, circles, rectangles, general polygons and other methods.

In further forms, the part to be inspected is placed on a first conveyor which moves the part to be inspected into a first inspection position for illumination by the first light source. After inspection, the first conveyor preferably delivers the part to a second conveyor, with the part rotated or flipped so as to be viewed on a second side or surface, which moves the part into a second inspection region under the second light source for inspection by the second camera.

In one preferred form, the conveyor includes a belt with a minimum light reflectivity in order to minimize the secondary light reflections from the belt.

In order to track the position of the part on the conveyors, each conveyor preferably includes an encoder, which is coupled to and in communication with the computer. The encoders generate periodic pulses as the conveyors move. Each pulse generated by the encoder represents a fixed distance of movement of the respective conveyor.

In other forms, to reduce data acquisition time and analysis time, a sensor which is in communication with the computer, is positioned at or near the respective inspection locations on the conveyors. When a sensor detects a part, the sensor generates a signal to the computer which initiates the data acquisition and analysis process. For example, the sensor may comprise a fiber-optic-through-beam sensor. The fiber-optic-through-beam sensor generates a beam that preferably extends across the conveyor. When the beam is interrupted, the sensor generates a signal which signal triggers the computer software program to initiate the acquisition and analysis sequence. Preferably, the software is programmed to sample a preselected number of signals from the camera following the trigger of the sensor. In this manner, the number of blank lines or invalid readings are reduced.

In preferred forms, the cameras are positioned to have the same general orientation with respect to the structured lighting light source. In this manner, both sides of the part are inspected, one at each station. By viewing the parts from opposite sides but at approximately the same elevation angle, the shadowing effects experienced by the cameras are negated and, together, the cameras view the entire part.

Each of the cameras views the laser line at an angle. Those skilled in the art of using structured light will recognize that some portions of some profiles of a part may be obscured by the part itself, owing to this angle of view. In these cases, a second camera viewing the part from the opposite side of the light line may be able to view the profile without this shadowing effect. Then the profiles can be combined and the effects of shadowing reduced or eliminated. In cases where surfaces of parts show little or no shadowing, such as diaphragms, there may be no advantage to this method while in other cases, such as rotary seals, this method may be helpful.

In yet another aspect of the invention, the inspection system includes a pair of 2-D cameras, which can be used to inspect a part, either before or after the 3-D inspection stations. In this manner, the 2-D cameras may provide another check for lateral dimensional conformity and may provide better inspection of parts that have deep or narrow structures, such as sidewalls.

In further forms, the inspection system includes a removal mechanism when a defective part is detected. Removal can be initiated at the camera or at some other location. In which case, in order to track a defective part, the system may include, for example, a shift register. When the software determines that a part is defective, the software sets a "defective bit" in the shift register. As the conveyor moves, the shift register moves this "defective bit" along to the next bit after some number of counts from the encoder. In this manner, the time between inspection and removal can be adjusted. Optionally, the period between detection of a defective part and removal may be selected by the user.

These and other objects, advantages, purposes and features of the invention will become more apparent from the study of the following description taken in conjunction with the drawings.

DETAILED DESCRIPTION OF THE PREFERRED EMBODIMENTS

Figure 1:
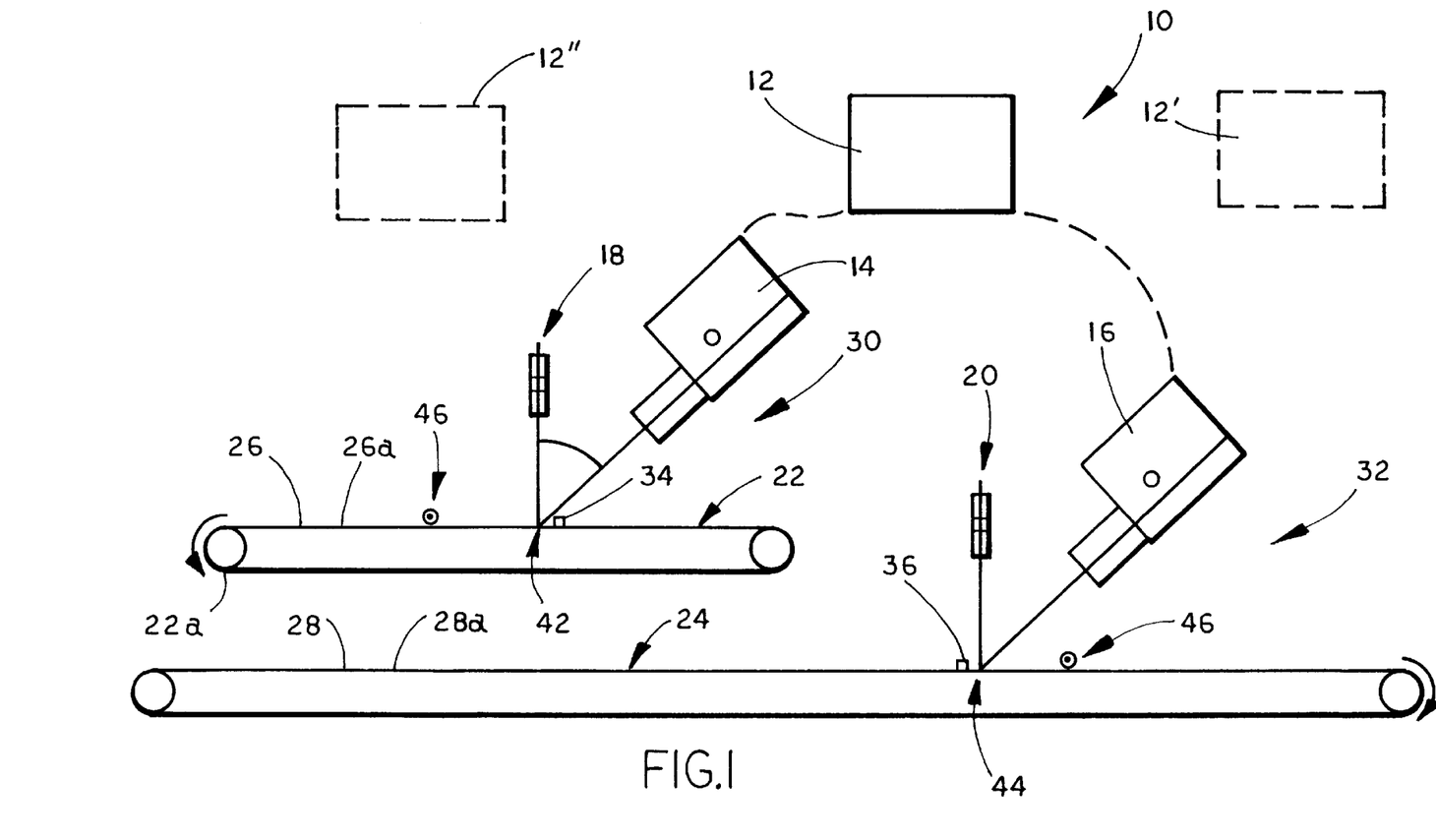
FIG. 1 is a schematic side elevation view of the inspection system of the present invention.

Referring to FIG. 1, the numeral 10 generally designates an inspection system of the present invention. Inspection system 10 includes a computer 12, which is in communication with a pair of cameras 14 and 16, and a pair of light sources 18 and 20. In a preferred form, inspection system 10 is used for inspecting parts on first and second conveyors 22 and 24, as will be fully described below.

Inspection system 10 of the present invention is particularly suitable for inspecting circular parts, for example, transmission seals, grommets, actuator diaphragms and the like. These parts may be metal, coated metal, plastic, or polymeric materials, composite materials and the like, or combinations thereof. Inspection system 10 is a three-dimensional inspection system which is easy to use and can be programmed to inspect a wide variety of parts. In addition, inspection system 10 approaches the level of inspection that is achieved using human inspectors and, furthermore, can achieve inspection of parts at a rate of one to two parts per second, using the methods or processes described below.

In preferred form, cameras 14 and 16 are high speed cameras which are used to profile the various parts so that the profiles of each known good part to be inspected can be stored in the computer for later comparison with the actual inspection data. For example, a high speed camera suitable for the present invention includes IVP Model MAPP2200 System available from IVP of Sweden.

Light sources 18 and 20 generate structured lighting, for example, a line of light. Light sources 18 and 20 for example, may comprise laser line generators, such as available from Laseris, Inc., of St. Laurent, Quebec, Canada, which ensure that adequate light is available in a very short period of time to accommodate the desired inspection speed. Referring to FIG. 1, a light line generated by light sources 18 and 20 is projected straight down onto the respective conveyors 22 and 24, while cameras 14 and 16 view the light line on the part. In order to inspect the entire part, cameras 14 and 16 view the line of light on opposite sides of the part respectively and at a range of approximately 30° to 60° in elevation. Preferably, cameras 14 and 16 are oriented at the same angle but view the part from opposite sides and together cameras 14 and 16 view the entire part.

Cameras 14 and 16 view the reflected light from the part and generate profile signals which are forwarded to computer 12 so that the computer 12 can analyze the profile signals and generate a height image of the inspected part. Preferably, the height image of the inspected part is analyzed by comparing it to known good part data taken under similar conditions. As will be more fully described in reference to the method of inspection, known good part data can be downloaded into the computer or can be generated by the computer. Furthermore, the "profiles" can be analyzed by other known methods. Computer 12 evaluates the differences between the part under test and the known good part data and preferably compares the differences to inspection parameters stored in the computer or input into the computer by the operator, in order to determine whether the inspected part is satisfactory or unacceptably defective. The method used by computer 12 for gathering the individual profiles is well-known and is outlined in the technical publication Smart Image Sensors, Linköping Studies in Science and Technology Dissertations No. 319, Linköping University, Linköping, Sweden (1993).

In the preferred form, inspection system 10 includes two inspection stations 30 and 32. Each inspection station 30, 32 includes a respective camera 14, 16, a respective light source 18, 20, and a respective conveyor 22, 24. Preferably, each inspection station 30, 32 further includes a part in place sensor 34 and 36 which is coupled to or in communication with computer 12. Sensors 34, 36 detect when a part enters the region of inspection. For example, sensors 34, 36 may comprise fiber-optic-through-beam sensors. Preferably, sensors 34 and 36 generate a beam across the respective conveyor belts of conveyors 22 and 24. Most preferably, the sensors 34 and 36 direct beams across conveyors 22 and 24 in close proximity to the region of inspection. Furthermore, sensors 34 and 36 generate a beam which is directed across conveyor 22 and 24 at or near the conveyor belt upper surface 26a and 28a. Therefore, when the beam is broken, sensors 34 and 36 indicate that a part is in place for inspection by the respective camera 14, 16. For example, sensors 34 and 36 may generate a signal when the beam is broken. Preferably, sensors 34 and 36 generate an "in-place" trigger signal to computer 12, which initiates a sequence of inspecting the part that is in the region of inspection. To assure good data, computer 12 is programmed to analyze a fixed number of profiles following the trigger signal. Optionally, computer 12 is programmed to permit user defined distances between the part in place sensor and the light source to avoid gathering of invalid profiles or blank lines. In this manner, the data acquisition mode can be delayed until the part is actually in line with the light source 18, 20, as will be more fully described below. Once the profiles are gathered, computer 12 begins the analysis. Preferably, computer 12 gathers sufficient data for analysis within approximately 0.5 seconds. Furthermore, the computer preferably completes the analysis in approximately 0.6 seconds. In this manner, the spacing between the parts to be inspected can be reduced to optimize the inspection rate. For example, in preferred form, the distance between parts to be inspected is approximately equal to the diameter of the parts.

Figure 2:
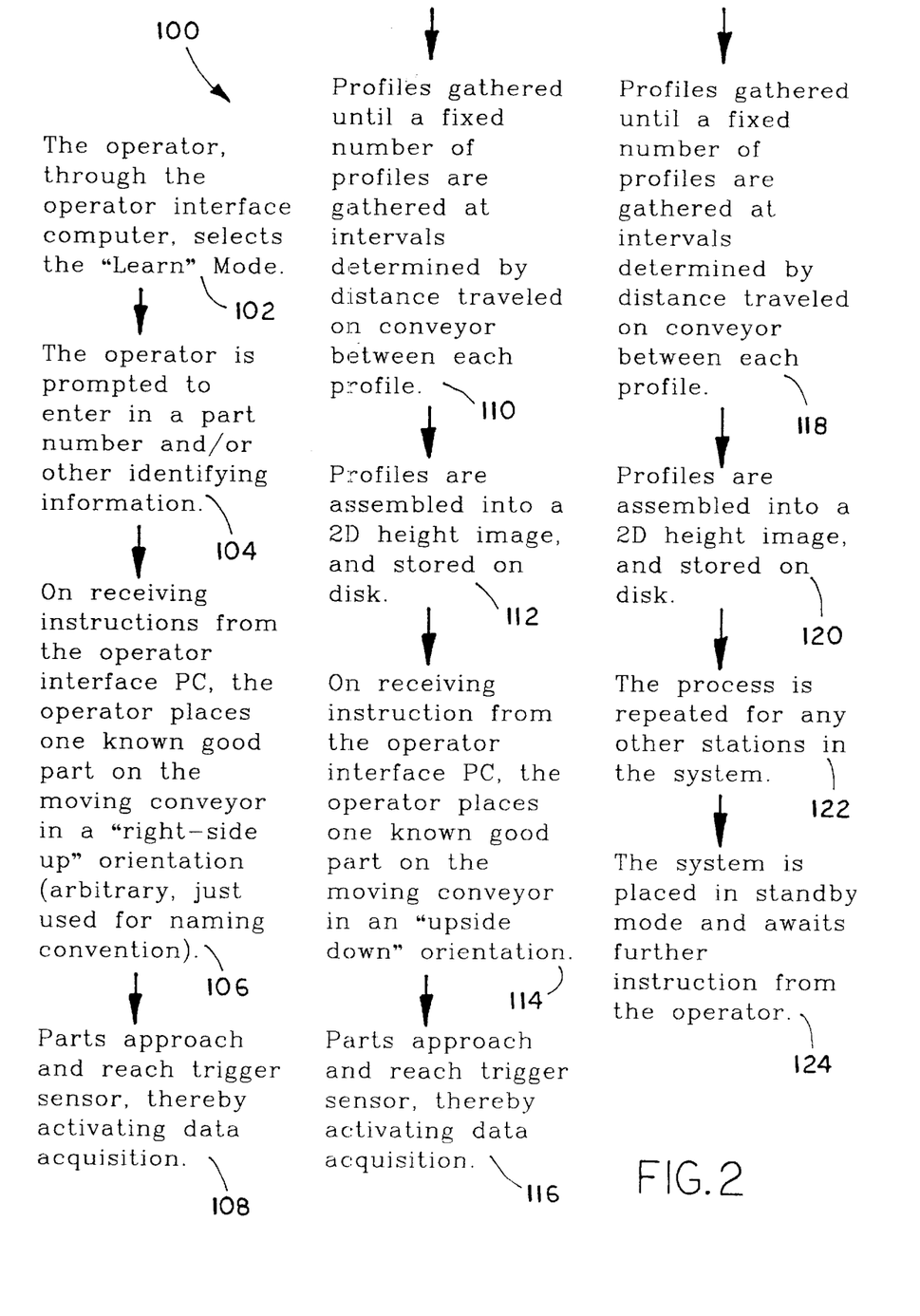
FIG. 2 is a flow diagram illustrating a learning mode of operation of the inspection system of the present invention.

Data acquisition and analysis may be accelerated by reducing the amount of data transfer required between the computer and the camera. Preferably, known good parts are inspected by inspection system 10 and their respective profiles are stored in the computer (FIG. 2). When profiling the known good part, the part shows regions where the part exists and regions where it does not. By using the profile gathered using all the part data during a part learning procedure, a mask may be created to indicate whether certain portions of the profiles are likely to have actual part data or simply be blank. By guiding parts to be inspected to a location close to the original position of the known good part, for example, within about 1 millimeter of the original "taught" position the data transfer can be reduced to about half of the originally collected data for the known good part. In this manner, the speed of data acquisition and analysis is considerably increased which permits the acquisition and analysis times noted above to be achieved.

When the inspection process is initiated, conveyor 22 moves the part to be inspected toward the inspection region under camera 14, in the illustrated embodiment as viewed in FIG. 1, conveyor 22 moves the part from right to left. As the part crosses through the beam generated by sensor 34 into first inspection region 42, sensor 34 generates an in-place trigger signal to computer 12 to initiate the data acquisition process. The data acquisition process may include powering light source 18 and camera 14 and, further, may include a preprogrammed delay or operator-programmed delay before computer actually collects the profile data from camera 14. As previously described, light source 18 generates structured lighting and, more preferably, produces a line of light. The light line is projected down onto moving conveyor 22 and onto a first side of the part while camera 14 views the light line at an angle in a range of approximately 30° to 60° in elevation. In order to avoid secondary reflections of the light off the part and off belts 26 and 28, belts 26 and 28 are preferably selected to minimize reflected light intensity back to the respective camera 14, 16. This is especially important when inspecting shiny objects In order to ensure that profiles are determined at regular intervals and to track the location of parts on the conveyor, the inspection system includes an encoder for each respective conveyor 22 and 24. The encoders may be integrated with the conveyor motor or gear motor (not shown) or may be separate from the conveyor motor. The encoders generate pulses periodically as a function of the conveyors motion. In this manner, each pulse from the encoder represents a fixed distance of movement of the respective conveyor 22, 24. For example, the encoders may generate a pulse that represents about 0.0005 inches per pulse. By taking profiles after a fixed number of pulses, profiles are taken at regular intervals which ensures a good comparison between known good part height images and the images gathered of parts under inspection. Ideally, profiles analyzed by computer 12 are taken under similar conditions of known good parts. Therefore, the differences between the part under test and the known good part can be judged either as acceptable or unacceptable.

Referring again to FIG. 1, after a part has been inspected by inspection station 30, the part is rotated or flipped 180° to be inspected on its second side or in its second orientation. In the illustrated embodiment, the part is flipped over by conveyor 22. Conveyor 22 imparts forward motion to the part to be inspected; however, once the part is moved over the edge of 22a of conveyor 22, the forward motion of the part along with gravity cause the part to be deposited on upper surface 28a of belt 28 of conveyor 24 in a reverse or inverted position. It can be appreciated that other devices or methods can be used to flip the parts over. Conveyor 28 moves the part to the right (as viewed in FIG. 1) toward second inspection region 44. As the part approaches second inspection region 44, the part passes through the beam generated by sensor 36, which, in turn, generates an in-place or trigger signal to computer 12. As noted previously in reference to sensor 34, computer 12 may initiate the inspection process or delay the inspection process by a preprogrammed or operator-selected distance as measured by an encoder. Similar to light source 18, light source 20 projects a light line straight down onto conveyor 24, while camera 16 views the light on the part at an angle in a range of approximately 30° to 60° in elevation. Similar to camera 14, camera 16 views the profile of the light line on the part and forwards the profile data to computer 12, which subsequently analyzes the profile as outlined above. As described previously, cameras 14 and 16 view the parts under inspection and further from opposite directions; consequently, a portion of the part is clearly not visible to each respective cameras 14 and 16. Nevertheless, using two cameras, both sides of the part are inspected. This "shadowing" means that some areas cannot be inspected by the individual cameras. As noted, by using two additional cameras at each individual inspection station 30, 32, which view the part from opposite directions at approximately the same elevation angle, the shadowing is negated. As a result, the entire part is inspected.

In addition, an inspection system 10 may include a respective computer 12, 12' for each inspection station 30, 32. Preferably, computers 12 and 12' are networked so that the information collected by both computers could be shared and, moreover, so that inspection stations 30, 32 could be controlled by a single source. Furthermore, computers 12 and 12' may be networked with a separate operator interface computer 12". Interface computer 12" may be programmed to permit the operator to select, for example, the process to be initiated and the part number of the part to be inspected.

Optionally, inspection system 10 may be coupled with a conventional 2-D inspection system. In preferred form, the 2-D inspection system cameras view the parts to be inspected at a normal incidence (90° to the conveyor belt). As a result, the 2-D cameras can be used to provide another check for lateral dimension conformity. For example, the 2-D cameras may be used to inspect 2-D projections of parts that have deep and narrow structures, such as sidewalls.

In order to remove defective parts from the stream of parts, inspection system 10 preferably includes a defective part remover 46, such as a pusher, including a servo actuated pusher, pneumatic or electric cylinder, or the like. Preferably, each inspection station 30, 32 includes a defective part remover so that a part can be removed when computer 12 determines that the part is unacceptably defective. Defective part remover 46 may be located in the inspection regions 42 and 44 or may be downstream from the inspection regions; in which case, in order to track when a part is determined to be defective, inspection system 10 may include a software-based shift register approach to follow the part after inspection to a point where the defective part is to be removed. When the part is deemed defective, a "defective bit" is set in the shift register. As belt 26 or 28 moves, the shift register moves the bit along to the next bit after some number of counts from a respective encoder. Optionally, this may be adjustable by the user to permit variations of time between inspection and removal. Furthermore, the user may select a number of consecutive bits to be turned on. Therefore, when the bits are shifted a defined number of times, and the defective condition is set, the removal mechanism can be actuated upon the next shift. When all removal bits have been passed, activation of the remover ceases.

Preferably, inspection system 10 has parameters to which the differences between the inspected part and known good part data are compared. The parameters may be input into the computer on a part-by-part basis, as desired, or may be input as a default value that is overridden by either a part specific set of parameters or by parameters input by the operator. In addition to different parameters for different parts, the inspection system may have different parameters for different attributes, for example, a defective depth group of parameters that can be used to determine whether to accept or reject a defect in a part. For example, when defects are large in area but small in depth, it may be desirable to accept the part nevertheless.

FIG. 2 is a flow chart detailing one method of inputting known good part data into computer 12 or process "teaching" the inspection system 10 about a known good part. Teaching process (100) is initiated by the operator of the system selecting a "Learn" mode (102). Computer 12 then prompts the operator to enter a part number and/or other part identifying information (104). After receiving instructions from computer 12, the operator places a known good part on conveyor 22 in a "right side up" orientation (106). It should be understood that this orientation is arbitrary and is just used as a naming convention. Henceforth, computer 12 understands that for a right side up orientation for this particular part, the particular part being inspected should have a certain height image and configuration.

Once placed on conveyor 22, the part approaches and reaches sensor 34 which generates a trigger signal to computer 12 to activate the data acquisition process (108). Computer 12 then gathers profile information until a fixed number of profiles are gathered at intervals which are determined by the distance the part travels on conveyor 22 between each profile (110). As noted previously, the distance traveled on the conveyor may be measured by an encoder. After computer 12 gathers the profile, computer 12 assembles the profiles into a 2-D height image and stores the information on the computer disk (112). After the known good part is evaluated for its right side up orientation, computer 12 instructs the operator to place the part on conveyor 22 in an "upside down" (114) orientation. This reference to orientation is arbitrary and is used as a naming convention only. Again, the part approaches and reaches the sensor 34 which, in turn, generates a trigger signal for computer 12 to activate the data acquisition process (116). Computer 12 the gathers profile signals generated by camera 14 until a fixed number of profiles are obtained. The profiles are obtained at intervals determined by the distance traveled by the part on conveyor 22 (118). Computer 12 assembles the profiles into a 2-D height image and stores the 2-D height image for the upside down orientation on the computer disk (120). This process may be repeated for any other stations in the system to ensure that each of the stations in the system include the known good part information (122). After completing the "Learn mode" the system is placed in the "standby mode" and awaits further instruction from the operator (124). It should be understood that the "learning" process can also be performed on conveyor 24. In the preferred embodiment, each camera 14, 16 has it's own computer 12, 12' for data gathering from the respective camera 14, 16 and analysis of the data. The third computer 12" may be then used for reporting results from each of the cameras 14, 16, determining whether each of the "analysis" computers 12, 12' is in standby, run or learn modes, storing the profiles of various parts and downloading these data to the respective analysis computers when the operator calls up a part number, or records these data if the operator is teaching new parts into the system via the "Learn" mode.

Figure 3:
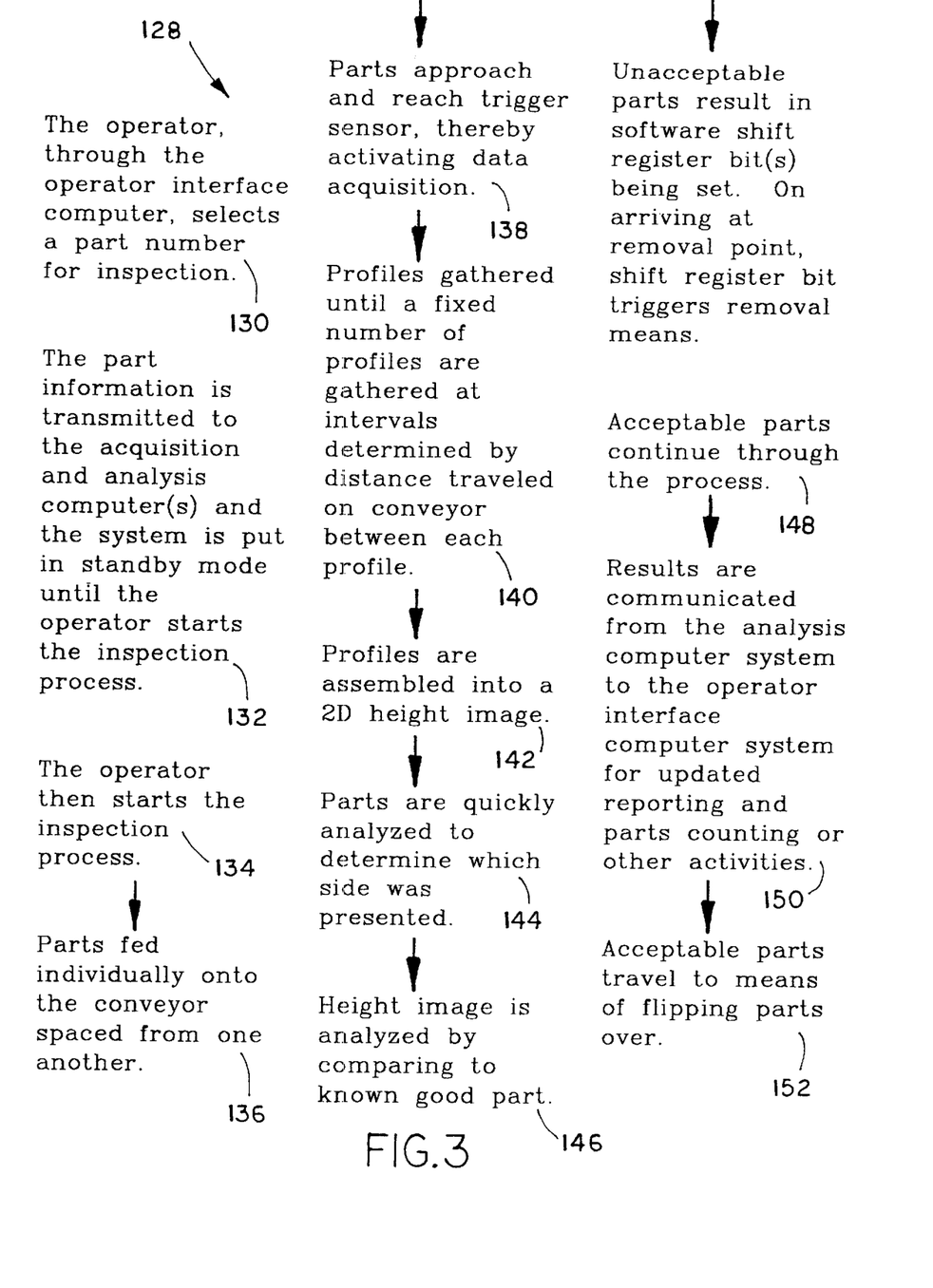
FIG. 3 is a flow diagram illustrating an inspection mode of operation of the inspection system of the present invention.
Figure 3A:
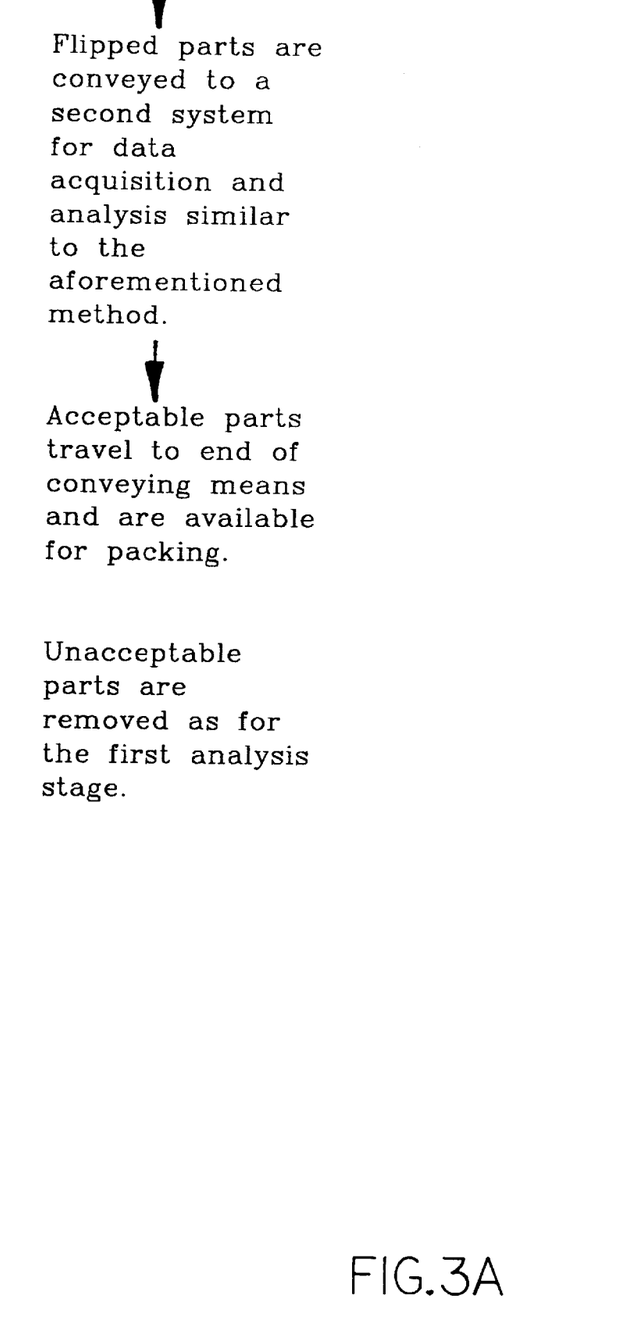

FIG. 3 is a flowchart detailing an inspection or process 130 mode for computer 12. In the "inspection mode," the unknown part is inspected by inspection system 10 and then compared to the known good part data for that particular part. Preferably in the "inspection mode," the number of profiles taken on the unknown part are optimized such that only those portions of the profile which yield meaningful data are taken. As a result, the amount of data transfer between cameras 14, 16 and computer 12 may be reduced, thus increasing the speed of the profile acquisition. In addition, by reducing the number of profiles taken, the required number of computations in the analysis phase of the inspection are likewise reduced. Ideally, the amount of data transferred from cameras 14 and 16 to computer 12 may be reduced by a factor of 2, which results in doubling the speed of the profile acquisition and analysis process.

Referring again to FIG. 3, the "inspection mode" process 128 is initiated by the operator. The operator selects the part number for inspection and inputs the part number into computer 12 (130). After the part information is input into computer 12, the operator places computer 12 in a standby mode until the operator is ready for the inspection process to initiate (132). Once the operator is ready, the operator starts the inspection process (134). The operator individually feeds parts onto conveyor 22 at spaced intervals (136). As the part approaches and reaches sensor 34, sensor 34 generates a trigger signal to computer 12 to thereby activate the data acquisition process (138). Computer 12 gathers or collects profiles at intervals determined by the distance the part travels on conveyor 22 (140). After collecting a preselected number of profiles, computer 12 generates a 2-D height image (142). Initially, computer 12 analyzes the 2-D image height by comparing the 2-D image height with the known good part data to determine which side was presented (144).

Typical parts feeding systems cannot be relied on to feed a variety of circular, disk-like seals with the same side up every time. In fact, even parts that are seemingly identical one side to the other may not, in fact, analyze that way. For example, if parts have small protrusions on one side only, the entire part will appear, in the present method, to be higher on one side than on the other. This is a manifestation of the 3-D analysis. Therefore, the software method of the present invention incorporates a scheme whereby the parts are determined to be either right side up or upside down. As previously noted, these terms are arbitrary and are used for a naming convention only. Software then incorporates this feature making it unnecessary to feed parts of the one side or the other. After determining whether the part was right side up or upside down, computer 12 analyzes the part by comparing the profile to known good part data (146). If computer 12 determines that the part analyzed deviates from the known good part data and that the deviations exceed the parameters for the given part, computer 12 sets the shift register to indicate a defective part. Once the part reaches a removal point, the shift register bit initiates the computer to actuate the remover while acceptable parts continue along conveyor 22 (148).

Optionally, inspection system 10 may include a report and inventory system. In which case, the inspection results are communicated from the analysis portion of the computer system to the operator interface computer system for updating reporting and parts counting or other activities (150). After inspecting one side of the part, the part continues travel along conveyor 22 until it is flipped over onto conveyor 24 (152). The parts are conveyed along conveyor 24 to second inspection station 44 for further data acquisition analysis similar to steps 138–146. After passing through the second inspection station 32, acceptable parts travel to the end of conveyor 24 and are ready and available for packing. In a similar manner to step 148, unacceptable parts are removed by remover 46.

Many improvements and variations are expected to be understood by those skilled in the art of machine vision inspection, particularly those familiar with three-dimensional inspection. Some improvements may include using various types of cameras, including, for example, analog or digital cameras, with addressable or non-addressable configurations. Also, the light source may include single or multiple line lights or other geometries of projected structured light, including but not limited to dots, radial lines, chevron lines, circles, rectangles, general polygons and other methods. In the preferred embodiment, a single line of laser light is used for simplicity. While inspection with non-laser structure light is also possible, such as white light structured illumination; for example, Fostec Inc., the single line of laser light increases the speed of the inspection process and is therefore preferred. In addition, depth profiles can be achieved by using expanding circles of light and the like which would yield series of depth profiles at increasing radii. This information could be reassembled into a circularly symmetric image of the part under inspection. In addition, the system may be calibrated from typical "pixels" to real world units, such as square inches or square millimeters per area and inches or millimeters for linear measures and the like. Furthermore, inspection system 10 may be configured to take data directly from the customer in some form such as a CAD part drawing or other forms of data. These and other variations are also contemplated.

Furthermore, while several forms of the invention have been shown and described, other forms will now become apparent to those skilled in the art. The embodiments of the invention shown and described are not intended to limit the scope of the invention which is defined by the claims which follow.

The embodiments of the invention in which We claim an exclusive property or privilege are as follows:

1. An inspection system for inspecting circular parts, the inspecting system comprising:
   a light source;
   a camera; and
   a computer, said computer in communication with said camera and having stored therein known good part profile data, said light source for directing light onto the part to be inspected, said camera generating profile signals in response to the light on the part, said computer receiving said profile signals from said camera and assembling said profile signals into a height image of the part and, further, comparing the height image with said known good part profile data to determine whether the part is acceptable or unacceptable.

2. The inspection system according to claim 1, wherein said light source generates a structured light pattern.

3. The inspection system according to claim 2, wherein said structured light pattern comprises a line of light.

4. The inspection system according to claim 1, wherein said light source comprises a laser line generator.

5. The inspection system according to claim 1, wherein said camera comprises a high speed camera.

6. The inspection system according to claim 1, wherein said light source comprises a first light source and said camera comprises a first camera, said inspection system further comprising a second light source and a second camera, said computer in communication with said second light source and said second camera, said first camera generating profile signals in response to the light generated by said first light source on a first side of the part, said second camera generating profile signals in response to the light generated by said second light source on a second side of the part, and said computer receiving said profile signals from said first and second cameras and assembling said profile signals into said height image of the part and, further, comparing said height image with said known good part profile data to determine whether the part is acceptable or unacceptable.

7. The inspection system according to claim 6, wherein said computer is programmed to analyze the profile signals from said first camera to determine which side of the part was viewed by said first camera and to select from said known good part profile data the data which corresponds to the viewed side of the part.

8. The inspection system according to claim 1, wherein said inspection system includes an operator interface device permitting the operator to input a part identifier into said computer, said computer selecting known good part profile data corresponding to said part identifier for comparing said selected known good part profile data with said height image.

9. The inspection system according to claim 1, wherein said computer includes defect parameters stored therein, said computer comparing deviations between said height image and said known good part profile data with said defect parameters to determine whether said part is acceptable or unacceptable.

10. The inspection system according to claim 9, wherein said computer includes adjustable defect parameters stored therein.

11. The inspection system according to claim 1, further comprising a conveyor, said conveyor for supporting the circular parts during inspection.

12. The inspection system according to claim 11, further comprising a sensor, said light source and said camera being directed at an inspection region on said conveyor, said sensor detecting when a part enters said inspection region and being in communication with said computer, said computer initiating receiving of said profile signals from said camera and assembling said profile signals to form said height image in response to said sensor detecting a part entering said inspection region.

13. The inspection system according to claim 12, wherein said sensor comprises a fiber-optic-through-beam sensor, said fiber-optic-through-beam sensor generating a beam across said conveyor and generating a trigger signal to said computer when the part interrupts the beam.

14. An inspection system for inspecting circular parts, said inspection system comprising:
a first inspection station and a second inspection station, each of said inspection stations including a camera and a light source;
each of said inspection stations further including a respective computer associated and in communication with each of said cameras and said light sources, said light source of said first inspection station for directing light onto a first side of a part to be inspected, said camera of said first inspection station generating first-side profile signals in response to the light on the first side of the part, said computer receiving said first-side profile signals and comparing said first-side profile signals with said known good part profile data to determine whether the part is acceptable or defective; and
means for transferring the part from said first inspection station to said second inspection station, said light source of said second inspection station for directing light onto a second side of the part to be inspected, said camera of said second inspection station generating second-side profile signals in response to the light on the second side of the part, and said computer receiving said second-side profile signals from said camera in said second inspection station and comparing said second-side profile signals with said known good part profile data and analyzing whether the second side of the part is acceptable or unacceptable, wherein each of said computers gathers said profile signals from its associated camera and assembles height images based on said profile signals, and each of said respective computers comparing said height images to said known good part data for analyzing whether the part under inspection is acceptable or unacceptable.

15. The inspection system according to claim 14, wherein said light sources comprise structured light sources.

16. The inspection system according to claim 15, wherein said light sources comprise laser line generators.

17. The inspection system according to claim 14, further comprising a defective part remover, said defective part remover being actuated by said computer to remove a defective part from the respective inspection station in response to said computer determining one of the first and second sides of the part being unacceptable.

18. The inspection system according to claim 14, wherein said means for transporting the part from said first inspection station to said second inspection station comprises at least one conveyor.

19. The inspection system according to claim 18, wherein said conveyor section includes an encoder, said encoder being in communication with the computer and generating distance traveled signals as a function of the distance the conveyor moves, and said computer tracking the location of the part based on said distance traveled signals.

20. The inspection system according to claim 14, each of said inspection stations further including a part-in-place sensor to detect when a part is in close position for inspection by said light sources in said cameras.

21. The inspection system according to claim 14, further comprising a third computer, said third computer in communication with each of the computers of said inspection stations, said third computer storing said known good part data and downloading said known good part data to said computers of each of said inspection stations.

22. The inspection system according to claim 21, said third computer storing inspection parameters and downloading said inspection parameters to said computers of each of said inspection stations, said computers of each of said inspection stations analyzing the profile signals from the part under inspection based on said inspection parameters.

23. An inspection system for inspecting circular parts, said inspection system comprising:
a first inspection station and a second inspection station, said first inspection station including a first camera, a first light source, and a first computer in communication with said first camera, and said second inspection station including a second camera, a second light source, a second computer in communication with said second camera, said first light source for directing light onto a first side of a part to be inspected, said first camera generating first-side profile signals in response to the light on the first side of the part, and said first computer receiving said first-side profile signals and assembling said first-side profile signals into a first-side height image of the first side of the part and, further, comparing said first-side height image with said known good part profile data to determine whether the first side of the part is acceptable or defective;
a third computer in communication with said first and second computers, and said third computer storing said known good part data and downloading said known good part data to said first and second computers for a part under inspection; and
means for transferring the part from said first inspection station to said second inspection station, said second light source for directing light onto a second side of the part to be inspected, said second camera generating second-side profile signals in response to the light on the second side of the part, said second computer receiving said second-side profile signals from said second camera in said second inspection station and assembling said second-side profile signals into a second-side height image and, further, comparing said second-side height image with said known good part profile data and analyzing whether the second side of the part is acceptable or unacceptable.

24. The inspection system according to claim 23, further comprising a defective part remover, said defective part remover being actuated by a respective computer to remove a defective part from the respective inspection station in response to said respective computer determining one of the first and second sides of the part as being unacceptable.

25. The inspection system according to claim 23, wherein said means for transporting the part from said first inspection station to said second inspection station comprises at least one conveyor.

26. The inspection system according to claim 23, each of said first and second computers gathering profile signals from its associated first and second camera and assembling height images based on said profile signals, and each of said first and second computers comparing said height images to said known good part data for analyzing whether the part under inspection is acceptable or unacceptable.

27. The inspection system according to claim 23, said third computer storing inspection parameters and downloading said inspection parameters to said first and second computers said first and second computers analyzing the profile signals based on said inspection parameters.

28. A method of three-dimensional vision inspection for inspecting circular parts comprising the steps of:

directing structured light onto a first side of the part;

reading a profile of the light on the first side of the part with a camera;

providing a computer in communication with the camera;

gathering profiles from the camera and assembling them into a height image with the computer; and comparing the height image to known good part data for determining whether the part is defective with the computer.

29. The method of inspecting according to claim 28, wherein comparing the height image with known good part data includes determining deviations between said height image and said known good part data, and comparing said deviations to inspection parameters for determining whether the part is acceptable or unacceptable.

30. The method according to claim 29, further comprising providing adjustable parameters.

31. The method of inspecting according to claim 30, further comprising generating a part mask for a part, said part mask indicating where the part exists and regions where the part does not exist to reduce the amount of data processed by said computer.

32. The method according to claim 28, further comprising removing a part when it is determined that the part is defective.

* * * * *

UNITED STATES PATENT AND TRADEMARK OFFICE
CERTIFICATE OF CORRECTION

PATENT NO.   : 6,542,235 B1  
DATED        : April 1, 2003  
INVENTOR(S)  : Gregory T. Caskey and Angelo E. Cicone It is certified that error appears in the above-identified patent and that said Letters Patent is hereby corrected as shown below:

<u>Column 1,</u>  
Line 20, change "Material" to -- material --.

<u>Column 4,</u>  
Line 26, insert -- preferably -- after "20".

Signed and Sealed this

Fourth Day of April, 2006

JON W. DUDAS  
*Director of the United States Patent and Trademark Office*